United States Patent [19]
Levine et al.

[11] Patent Number: 5,321,975
[45] Date of Patent: Jun. 21, 1994

[54] DIFFERENTIAL ERYTHROCYTE COUNTS

[76] Inventors: Robert A. Levine, 31 Pilgrim La., Guilford, Conn. 06443; Stephen C. Wardlaw, 191 No. Cove Rd., Old Saybrook, Conn. 06475

[21] Appl. No.: 770,875

[22] Filed: Oct. 4, 1991

[51] Int. Cl.$^5$ .......................... G01N 33/48; A61B 5/14
[52] U.S. Cl. ...................... 73/61.71; 356/39; 436/70
[58] Field of Search ............... 73/61.4, 149, 61.1 R; 436/177, 70; 356/39

[56] References Cited

U.S. PATENT DOCUMENTS

| | | | |
|---|---|---|---|
| 3,437,266 | 4/1969 | Patterson | 210/361 |
| 4,082,085 | 4/1978 | Wardlaw et al. | 73/61.1 R |
| 4,209,226 | 6/1980 | Wardlaw et al. | 359/388 |
| 4,558,947 | 12/1985 | Wardlaw | 356/39 |
| 4,567,754 | 2/1986 | Wardlaw et al. | 73/61.4 |
| 4,835,097 | 5/1989 | Saunders | 436/70 |
| 4,843,869 | 7/1989 | Levine et al. | 73/61.4 |

OTHER PUBLICATIONS

Separation of Erythrocytes According to age on a simplified density gradient, 147–151, L. M. Corash, Jul. 1974.

*Primary Examiner*—Hezron E. Williams
*Assistant Examiner*—Michael J. Brock
*Attorney, Agent, or Firm*—William W. Jones

[57] ABSTRACT

Erythrocytes exist in vivo in a continuous cell subset gradient of density, with the youngest cells being the lightest. A blood sample is centrifuged in a transparent tube containing plastic beads which are selected to include groups of beads wherein each group has a different sharply defined specific gravity, and which are distributed within the range of red cell densities. The beads form spaced well-defined bands in the erythrocyte layer, which bands form boundaries between the different cell subset layers. Measurements of the lengths of the different cell subset layers are then made to quantify the red cell subsets in the patient's blood.

12 Claims, 8 Drawing Sheets

DIFFERENTIAL ERYTHROCYTE COUNTS

TECHNICAL FIELD

This invention relates to erythrocyte, or red cell, analysis in a sample of blood, and more particularly to a procedure and paraphenalia for determining the population frequency distribution analysis of density subsets of erythrocytes in a sample of blood, which analysis can mirror the historical formation and/or loss of red cells in a patient's blood for as much as the previous one hundred twenty days.

BACKGROUND ART

Presently, a patient's red cell concentration in the blood, which is the net of production-loss, is monitored by measuring the hematocrit count in the patient's blood. The hematocrit is the percentage volume that packed red blood cells occupy in a centrifuged sample of whole blood. Hematocrit determinations may presently be performed by filling a small bore glass tube with anticoagulated whole blood, sealing one end of the tube, and centrifuging the tube to pack the red blood cells. After packing, which takes about three to five minutes in a small centrifuge, the length of the packed red blood cell column and the total filled length are measured, and the hematocrit, expressed as a percentage, is calculated. The hematocrit determination gives no information as to red cell production and/or loss.

U.S. Pat. Nos. 4,027,660; 4,181,609; 4,156,570; 4,558,947; and others describe a procedure which involves drawing a sample of anticoagulated whole blood into a capillary tube, placing a float in the tube with the blood sample, and centrifuging the blood sample to cause the float to settle into the red cell layer, and allow differential buffy coat constituent counts to be measured. This technique is also used to measure hematocrit by applying a correction factor to account for the sinking of the float into the packed red cells, and can account for the shrinking of the packed red cells by any additives in the blood sample, such as potassium oxalate, if present. The hematocrit count is a reliable procedure for measuring the red cell content of the blood at the time the measurement is made, but it may not detect certain conditions relating to production of new red blood cells, or the loss of red blood cells. If the hematocrit is low, the physician will be alerted to the fact that a current condition exists which is either supressing new red blood cell formation; or that an atypical loss of red blood cells has occurred or is ongoing with insufficient increased production of red cells. Hematocrit determinations cannot, however, detect such atypical conditions unless they are relatively concurrent with the time the hematocrit is read. Thus, for example, if a patient has experienced a bleeding episode three weeks before the hematocrit is read, the blood test will not necessarily reveal the episode since the loss of blood may have caused increased red cell production to compensate for the bleed.

Red cells that are one day old maintain fragments of nucleic acid which, when stained with new methylene blue, cause them to appear as reticulocytes. By staining a smear of red blood cells, and then manually counting the percentage of red cells that are reticulocyes, one can estimate the present red cell production rate. Alternatively, reticulocytes may be enumerated in a blood sample with commercially available stains wherein the cells are detected and counted by fluorescent activated cell sorters (FACS). Neither the normal stain and smear procedure nor the FACS will be able to detect, for example: a red cell production rate that is five times the normal rate; which lasted for three days; and which increased production took place ten days prior to the blood sampling. These prior art procedures can detect increased or decreased production episodes only during the episodes, or for one day thereafter.

L. M. Corash et al, in the July, 1974 issue of The Journal of Clinical Medicine describe a procedure for separating erythrocytes according to age on a simplified density gradient. This publication states that age-dependent separation of erythrocytes may be accomplished by a variety of prior art cell supporting substances such as: bovine serum albumin; phthalate esters; dextran; and gum acacia. The publication states that these prior art procedures are undesirable and suggests that an arabino galactan polysaccharide of 30,000 daltons be used in lieu of the prior art supporting substances. The Corash et al procedure however requires the use of defibrinated, washed, and packed human erythrocytes which are layered on top of a performed medium gradient.

The tube containing the packed cells and medium is filled with mineral oil and then centrifuged to obtain the separation of cells. Thus the Corash et al procedure is time consuming and complicated.

DISCLOSURE OF THE INVENTION

This invention relates to a procedure and paraphenalia for performing red blood cell analyses, which produces a population frequency distribution analysis of density subsets of erythrocytes in a whole blood sample, which analysis can reveal the occurrence of increased and/or decreased red cell production episodes that have occurred during or prior to two days before the sample analysis and during the period of up to about one hundred twenty days before the analysis is performed, and which would not be revealed by the hematocrit and reticulocyte determinations performed in accordance with the prior art techniques.

Erythrocytes in vivo exist in a continuous gradient of density subsets, with the youngest being the lightest. This is due, in part, to a slow and progressive loss of cell potassium and water content concomitant with aging of the erythrocyte cells. The range of specific gravities of the total erythrocyte population is from about 1.050 to about 1.150; or up to 10% higher when red cell densifying agents are present in the sample.

This invention utilizes different density markers which are introduced into the centrifuge tube to delineate subsets of the erythrocyte population according to their specific gravity or density. An historic red cell analysis is thus possible which will be indicative of erythrocyte production (or loss) both normal and abnormal, over a time period of as much as one hundred twenty days prior to the date of the test.

The markers may be plastic beads, latex spheres, or lyposomes, or the like, which comprise fraternal groups, the bead or sphere marker components in each group having a sharply defined specific gravity which lies within the aforesaid range of erythrocyte specific gravities, and with the specific gravity of the markers in each group being different from the specific gravity of the markers in any other group. Preferably, there will be from five to twenty different groups of markers with evenly distributed specific gravity intervals between each group. Thus, for a twenty marker group embodiment, the marker specific gravity ladder will go from 1.050; to 1.055; to 1.060; and so forth, in 0.005 steps to 1.150; or a 10% higher range when a densifying agent is in the blood sample. The markers may be made by forming a solution of different plastics or other starting materials which have different densities or specific gravities. The markers will not have their densities or specific gravities altered by interaction with the blood cells or plasma present in the sample to be tested.

When the blood sample is centrifuged in the tube, the different groups of markers will settle out at the approximate interfaces between the erythrocyte population subsets, so that the lengths of each cell subset can be measured and converted to quantifications of the mass of erythrocyte density subsets. When the measurements are converted to a histogram, any abnormal erythrocyte production and loss which occurred prior to the test will be identified. If erythrocyte production and loss activity has been normal throughout the target time period prior to the test, then each of the erythrocyte subset layers or bands will have substantially equal lengths from the top of the red cell layer to the bottom, with a very gradual decrease in band length with increasing age due to physiologic blood loss. If abnormal erythrocyte production or loss has occurred during the previous target time period, then the band lengths will be shorter, or longer as the case may be.

For example, if a period of increased red cell production were to occur at a rate of about three (or any other multiple) times the normal physiologic rate, the affected red cell subset in the centrifuged blood sample will be increased in size. For example, if the red cell subsets are limited to cells from ten day periods, and if the increased production was present for five of the ten day subset period at three times the normal production rate (and, of course, if the sample were drawn during a time period wherein the subset was still present in the sample) the length of the subset would be twice the normal expected length. The aforesaid is illustrated by the following scenario of a ten day period during which normal red blood cell production is present for five days and abnormally high three-fold red blood cell production is present. Assume during any five days of the ten day period that three times the normal "unit" red cell production is present. During that period, fifteen (3×5) "units" of red blood cells are produced. For the other five days, five "units" of red blood cells (one "unit" for each of the five days) are produced. For the total ten day period one would expect to see ten "units" produced, but during the aforesaid abnormal production period, a total of twenty "units" will be produced. The abnormally high red cell production will therefore create an abnormally longer subset in the centrifuged red cell pack.

Likewise, obviously, if periods of decreased red blood cell production occur, the subset red cell band length will be less than expected.

During periods of prolonged blood loss due to bleeding, all red cell subsets present during the bleeding episode would be decreased by the same proportion.

It is therefore an object of the invention to provide an improved technique for assaying the red blood cell subset population in a sample of anticoagulated whole blood by density.

It is a further object of the invention to provide a technique of the character described wherein the red blood cells are centrifuged into a separate layer in a transparent tube and divided into visible subsets within the red cell layer.

It is yet another object of the invention to provide a technique of the character described wherein the red blood cell subsets are highlighted by adding markers to the blood sample, which markers comprise fraternal groups with each group having sharply defined and different densities or specific gravities.

It is an additional object to provide a technique of the character described wherein the markers are beads which form sharply defined lines in the red cell layer which delineate the red blood cell subsets by specific gravity.

These and other objects and advantages of the invention will become more readily apparent from the following detailed description of a preferred embodiment of this invention when taken in conjunction with the accompanying drawings in which:

DETAILED DESCRIPTION OF THE BEST MODE

Figure 1:
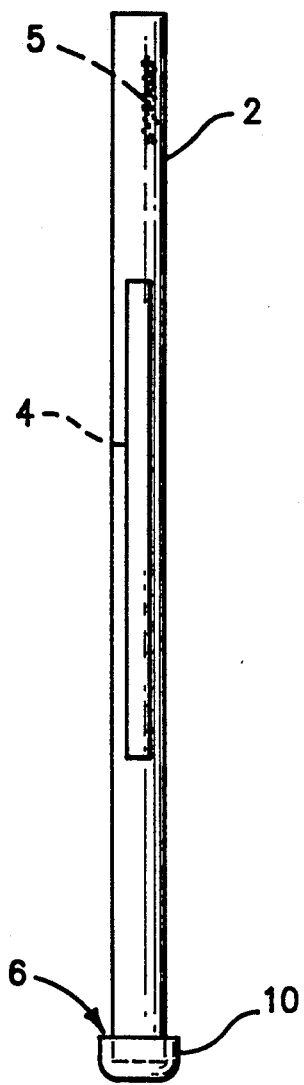
FIG. 1 is side elevational view of a centrifuge tube adapted to perform the procedure of this invention.
Figure 2:
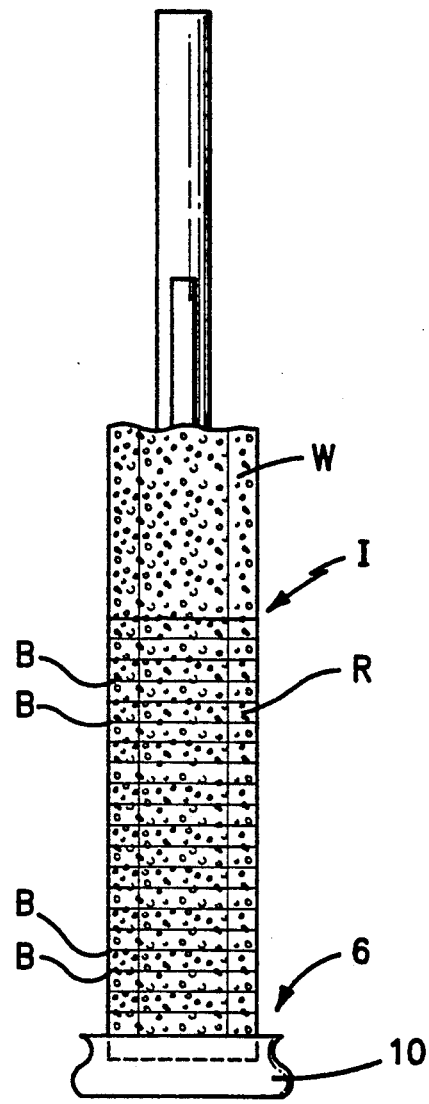
FIG. 2 is a view of the tube of FIG. 1 showing a centrifuged blood sample therein, and with the red blood cell layer being blown up or increased in size to particularly point out the nature of the invention.

Referring now to FIGS. 1 and 2, there is shown in FIG. 1, a tube 2, which may be a glass capillary tube, or other transparent tube, and which contains a float or insert 4 made of a plastic, which has a specific gravity that causes the float 4 to settle through the red blood cells to the bottom 6 of the tube 2 when the latter is centrifuged with the blood sample therein. The fraternal groups of plastic beads of different specific gravities may be disposed in a clump 5 in the tube 2. A plastic cap 10 closes the bottom 6 of the tube 2.

The blood sample is drawn into the tube 2 and centrifuged therein along with the float 4 and beads 5. The bead clump 5 disperses in the blood sample and settles into distinct bands which form lines in the red cell layer as shown in FIG. 2, while the float 4 settles into and through the red cells R.

The white cells W layer out in bands above a red cell/white cell interface I. The bead bands B divide the red cell layer into red cell subsets, which subsets are delineated by specific gravity, and therefore by age. Given normal red cell production and loss, each red cell subset will have a very gradually deminishing length as seen from the top of the red cell layer to the bottom.

Figure 3:
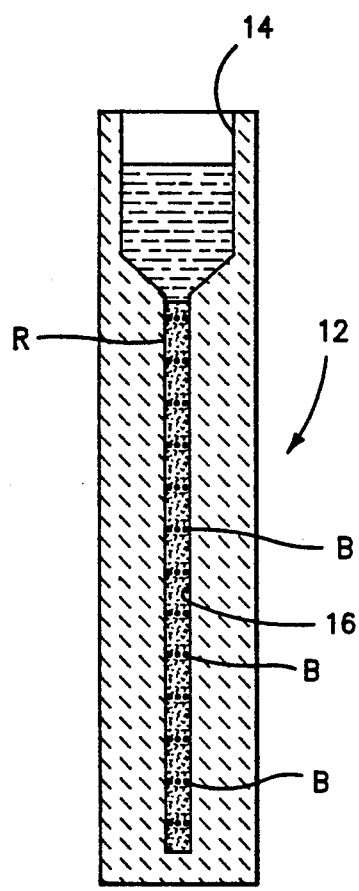
FIG. 3 is an axial sectional view of a second embodiment of a centrifuge tube adapted for use in performing the invention.

FIG. 3 shows an alternative form of centrifuge tube which can be used to practice the invention. The tube 12 has a compound funnel-shaped bore with an enlarged open end part 14 and a restricted closed end part 16. The bore is sized so as to cause the red cells R in the centrifuged blood sample to settle into the restricted 16 of the bore, with the white cells and plasma staying for the most part in the enlarged part 14 of the bore. The marker bands B disperse in the centrifuged red cell layer. The tube 12 is formed from a transparent glass or plastic material. It will be noted that the embodiment shown in FIG. 3 does not require a float component.

Figure 4:
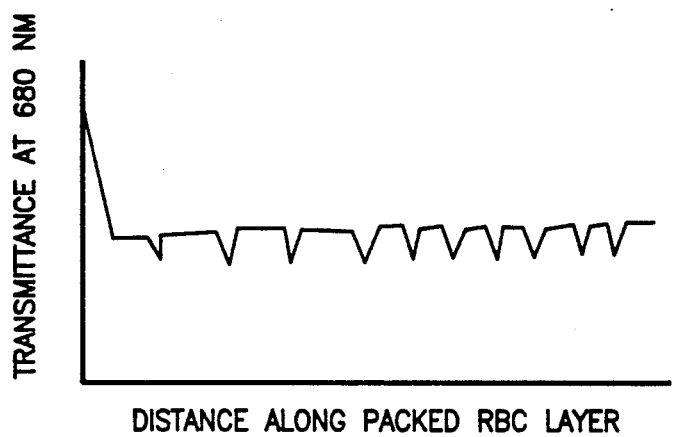
FIG. 4 is a schematic representation of a scan of the red cells in a centrifuged blood sample as made by a computerized reader instrument.
Figure 5:
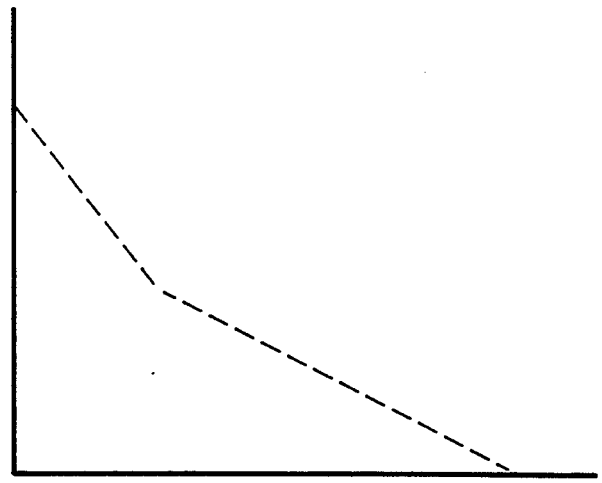
FIG. 5 is a generalized schematic representation of a bar chart printed from the cell subset layer thickness information derived from the scan.
Figure 6:
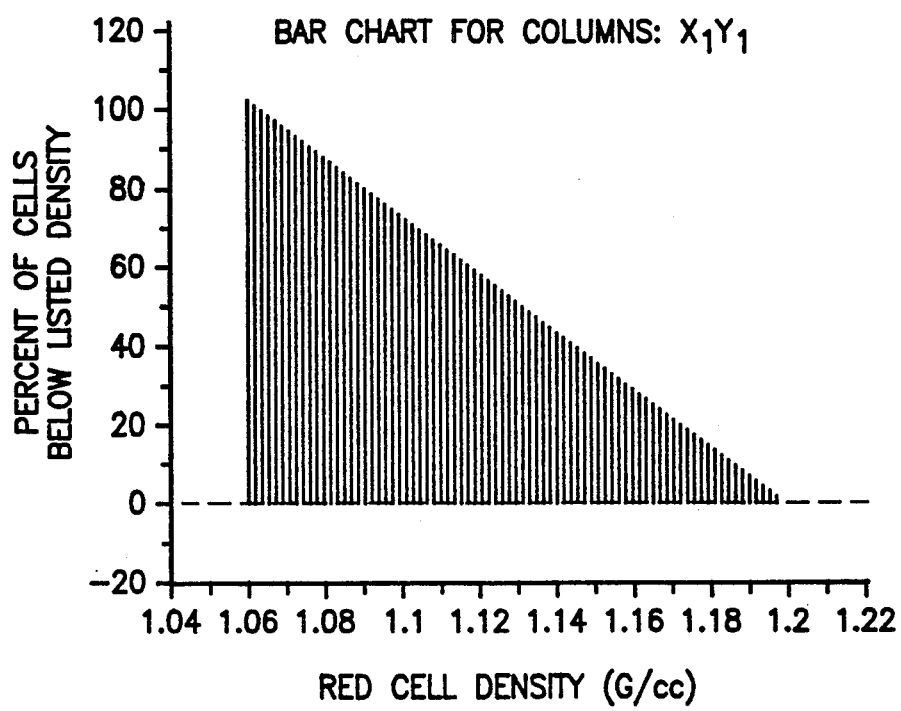
FIGS. 6–16 are bar charts of the red blood cell subset lengths showing normal and abnormal blood history.
Figure 7:
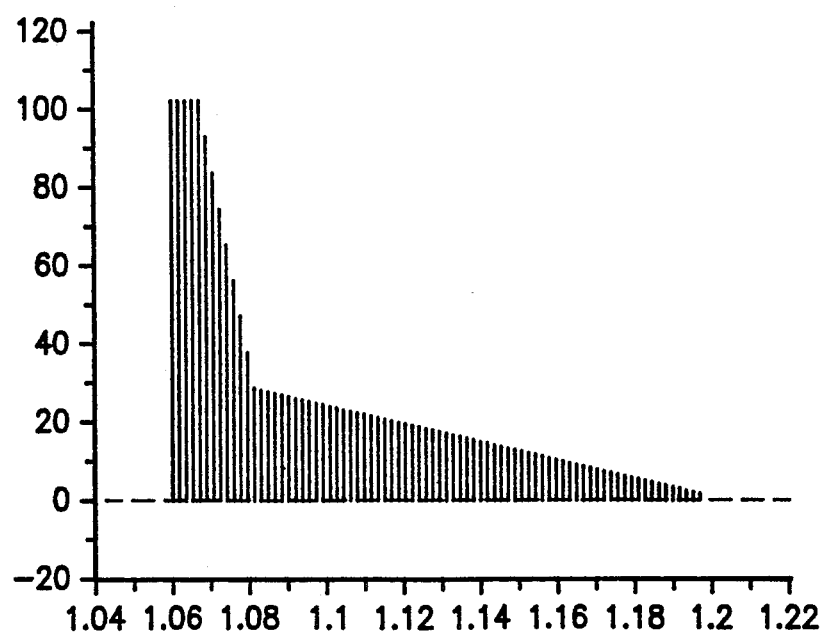
Figure 8:
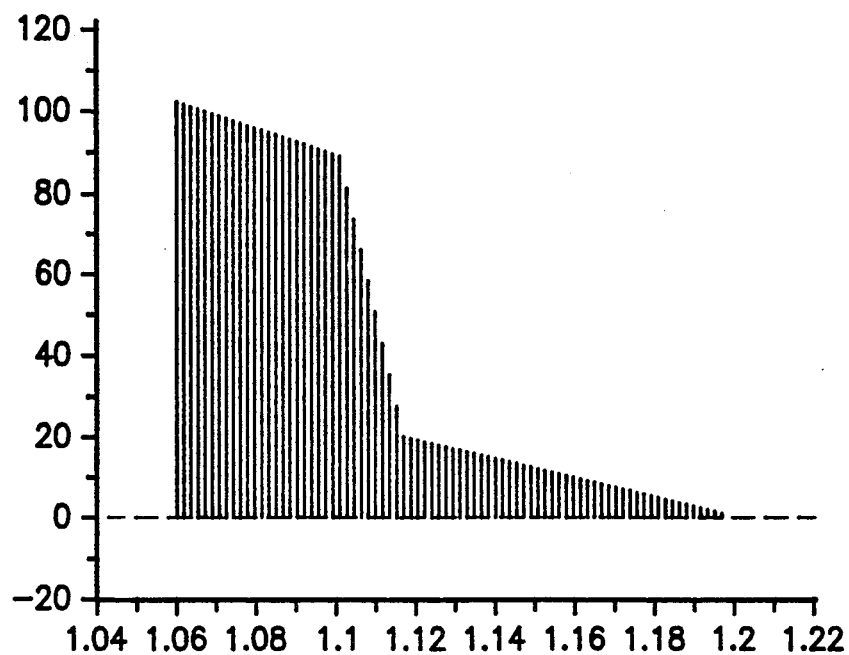
Figure 9:
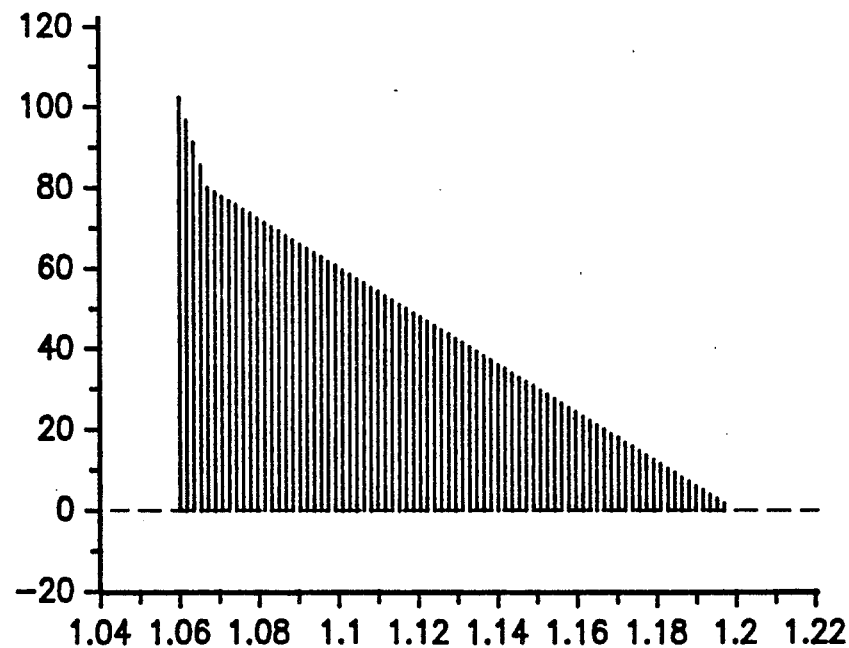
Figure 10:
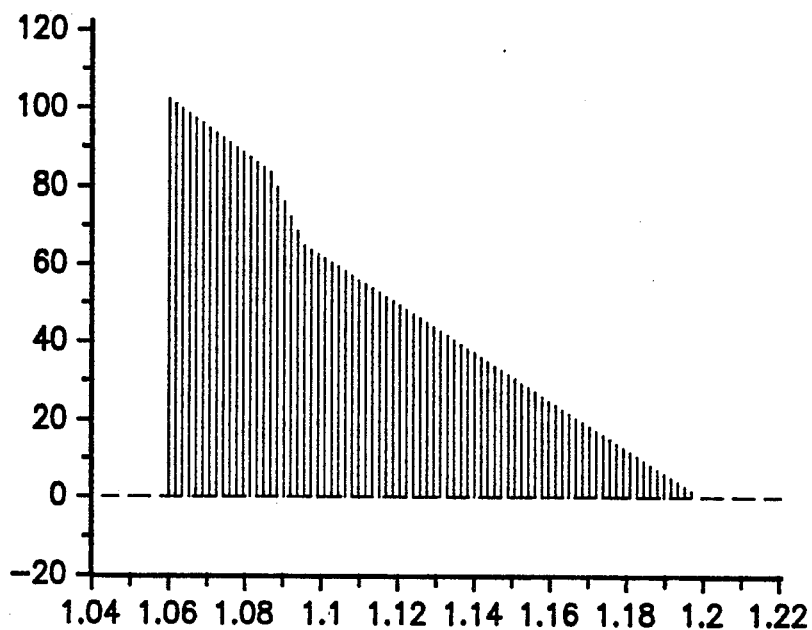
Figure 11:
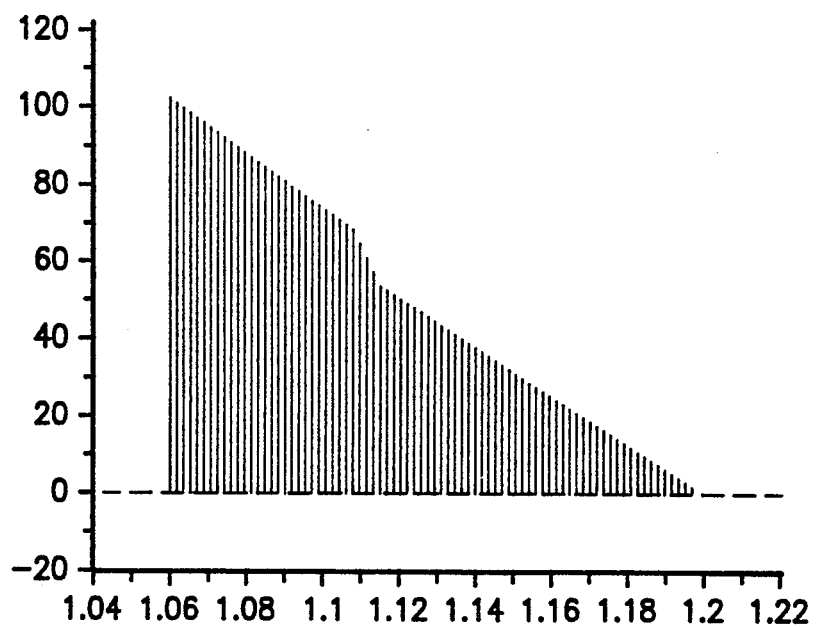
Figure 12:
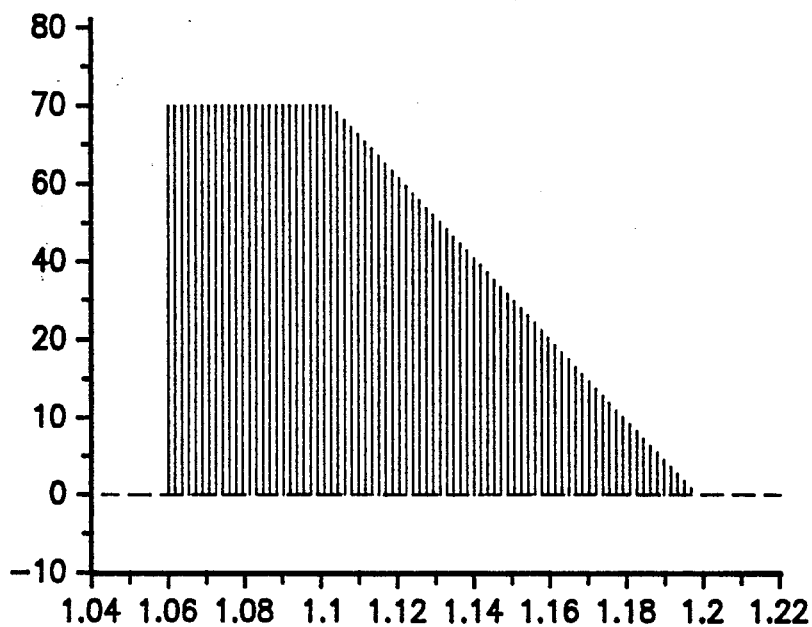
Figure 13:
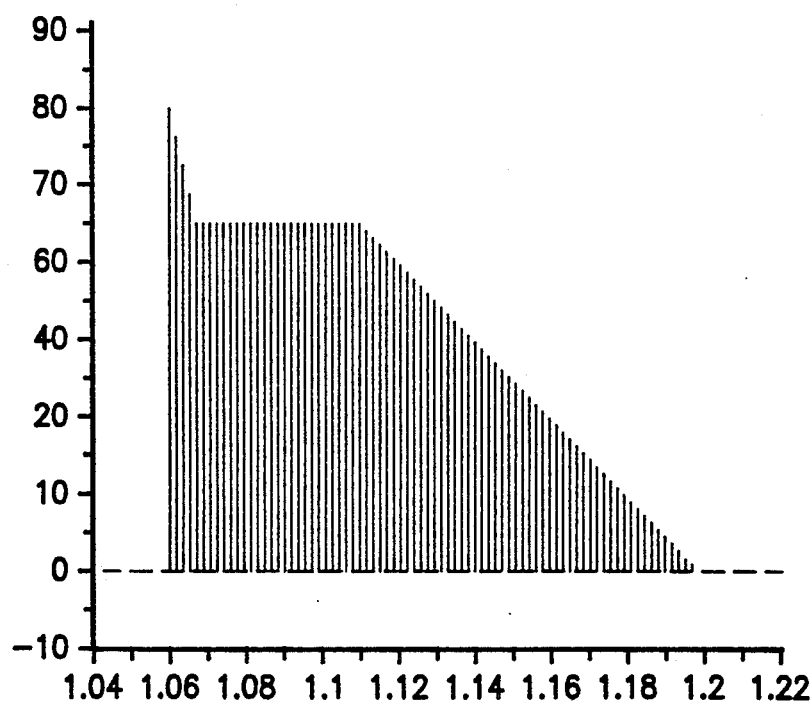
Figure 14:
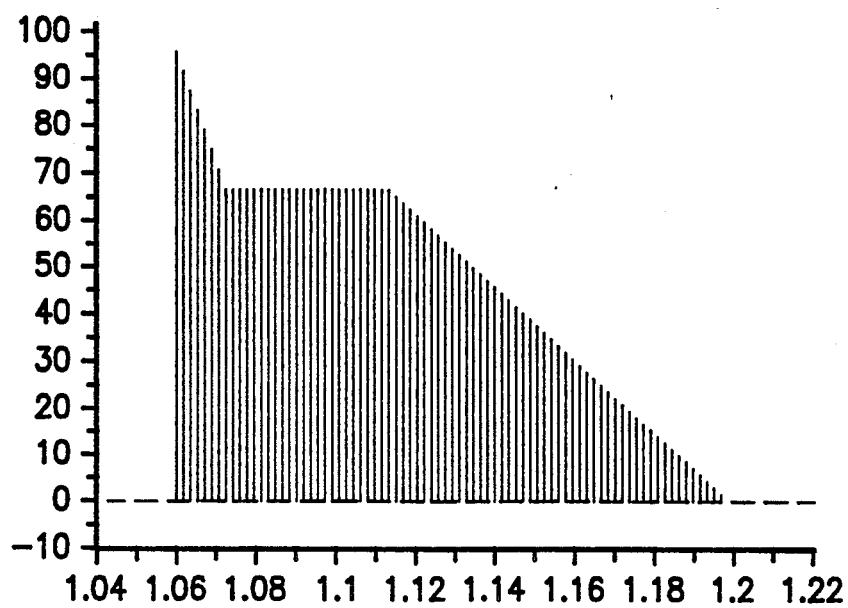
Figure 15:
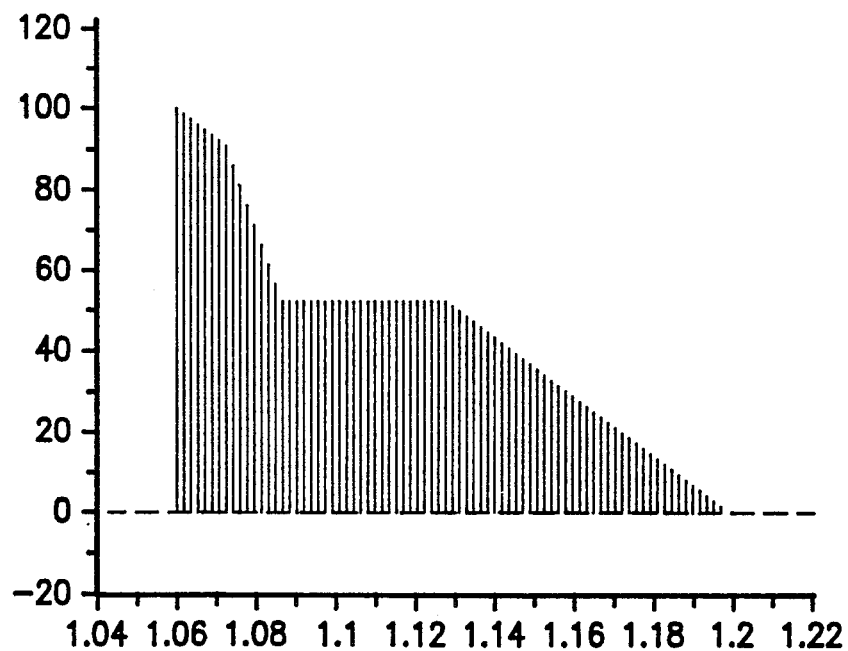
Figure 16:
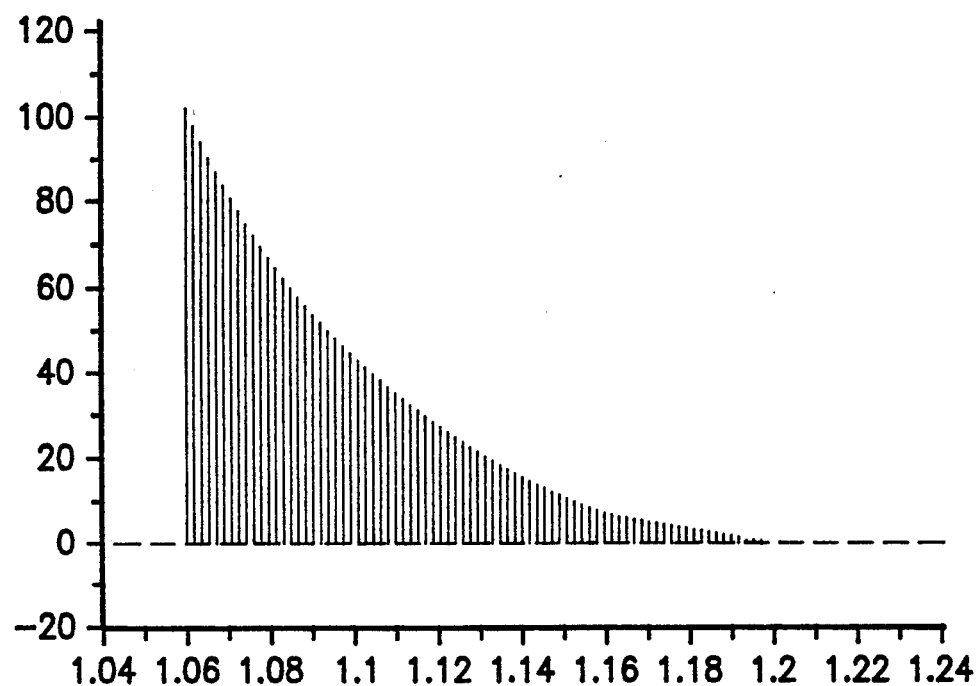

After the blood sample has been centrifuged, the sample is placed in an instrument of the type disclosed in U.S. Pat. Nos. 4,209,226 granted Jun. 24, 1980; or 4,558,947 granted Dec. 17, 1985 to S. C. Wardlaw. The instrument measures each of the red cell subset bands to produce a scan of the type shown schematically in FIG. 4, wherein the downwardly directed blips represent the marker bands or lines as "seen" by the instrument. That scan is converted into a bar chart histogram which is shown schematically in FIG. 5, wherein the X axis defines the red cell subsets by density (which reflect cell age), and wherein the Y axis is the percentage of the red cells which are disposed below the X axis cell densities in the red cell column.

FIGS. 6–16 are bar charts of the red blood cell subset lengths showing normal and abnormal results of the test with a marker subset group of one marker subset per day of history. The various conditions which each bar chart represents are identified in the individual figures. The bar charts effectively provide a daily histogram of the red cell layer which reveals historical red cell production and/or loss activity per day.

While the plastic insert may be described as "a float", it will be readily understood that it need not actually float in the red cells. The plastic insert should have a density or specific gravity which is sufficient to cause it to sink through at least a significant majority of the red cells, for example at least about 90% of the packed red cell column. The red cell subset layers should be expanded by a multiple in the range of about 1.5 to 3X. The length of the insert should be sufficient to ensure that it will extend completely through a packed red cell layer in a blood sample with an hematocrit of 40 or less. It will be appreciated that the insert could be formed as an integral part of the bottom plastic closure cap shown in FIG. 1 of the drawings.

The markers could comprise a plurality of disks formed from plastics having different densities or specific gravities; however, when such disks are used, they must be preloaded into the tube according to their densities or specific gravities, with the heaviest disks being positioned nearest the bottom of the tube and the lightest nearest the top.

It will also be appreciated that the time resolution of the procedure of this invention is dependent upon the number of marker subsets. For example, a one hundred twenty subset marker group, as are shown in FIGS. 6–16, will give a time resolution of one day; while a twelve subset marker group would give a time resolution of ten days under most conditions. The fact that the insert sinks completely through the red cell layer does not interfere with the ability to determine the hematocrit of the blood sample with an appropriate instrument as described in the prior art. Instruments which can be used to determine hematocrit in the blood sample are disclosed in U.S. Pat. Nos. 4,558,947 and 4,683,579, both granted to S. C. Wardlaw.

Since many changes and variations of the disclosed embodiment of the invention may be made without departing from the inventive concept, it is not intended to limit the invention otherwise than as required by the appended claims.

What is claimed is:

1. A method for performing a population frequency distribution analysis of density of subsets of erythrocytes in a sample of anticoagulated whole blood, said method comprising the steps of:
   a) providing a transparent tube containing the blood sample;
   b) providing a plurality of markers in said tube, which markers are defined by different densities within the density range of the erythrocytes, with each marker having a density which is distinctly different from the density of others of the markers; and
   c) centrifuging the blood and markers to separate the blood sample into its constituent layers by density, and to embed the markers in the erythrocyte layer so as to form distinguishable erythrocyte cell subset layers which layers are arranged by the density of the individual erythrocyte cells in the respective erythrocyte cell subsets, and which layers are bounded by spaced-apart detectable bands formed by said markers, which marker bands each have a density that is different from the erythrocyte cells on either side thereof.

2. The method of claim 1 comprising the further step of including a generally cylindrical insert in said tube, which insert has a specific gravity which will cause said insert to sink through the erythrocyte layer during said centrifuging step so as to increase the distance between adjacent marker bands in the erythrocyte layer.

3. The method of claim 2 comprising the further step of measuring the distance between adjacent marker bands to quantify the erythrocyte cell population in each erythrocyte cell subset layer.

4. The method of claim 3 comprising the further step of printing a histogram of the populations of said erythrocyte cell subset layers.

5. The method of claim 4 comprising the further step of determining historical red cell anomalies from said histogram.

6. The method of claim 1 wherein said markers comprise groups of plastic beads.

7. The method of claim 1 wherein said markers are plastic discs.

8. Paraphernalia for performing a population frequency distribution analysis of density of erythrocyte subsets in a sample of whole blood, said paraphernalia comprising:
   a) a transparent tube for containing the blood sample; and
   b) a plurality of markers, said markers each having a specific gravity within the specific gravity range of the erythrocytes, and with the specific gravity of individual ones of said markers being distinctly different from the specific gravity of other individual ones of said markers, and operable to form spaced apart bands in the erythrocyte layer, with the specific gravity of the markers forming each of said bands being different from the specific gravity of erythrocyte cells that will settle between said bands during centrifugation of the blood sample.

9. The paraphernalia of claim 8 wherein said markers are plastic beads.

10. The paraphernalia of claim 9 wherein said beads are divided into groups of beads wherein each group has a specific gravity which is about 0.005 different from the next adjacent bead group.

11. The paraphernalia of claim 8 further comprising a generally cylindrical insert for positioning in said tube, said insert having a specific gravity which will cause said insert to sink through an erythrocyte layer in a centrifuged sample of whole blood in the tube so as to separate adjacent bands of markers from each other.

12. The paraphernalia of claim 8 wherein said markers are plastic discs.

* * * * *